United States Patent [19]

Koyanagi et al.

[11] 4,273,769
[45] Jun. 16, 1981

[54] O-ETHYL S-ALKYL S-ISOPROPYL PHOSPHORO-DITHIOLATE, AND THEIR USE AS NEMATOCIDE

[75] Inventors: Rokuo Koyanagi, Ibaraki; Yoshio Fujita, Kawanishi; Kunio Mukai, Takarazuka, all of Japan

[73] Assignee: Sumitomo Chemical Company, Limited, Osaka, Japan

[21] Appl. No.: 139,990

[22] Filed: Apr. 14, 1980

[30] Foreign Application Priority Data

Apr. 20, 1979 [JP] Japan .................................. 54-49208

[51] Int. Cl.$^3$ ...................... A01N 57/12; C07F 9/165
[52] U.S. Cl. .................................... 424/224; 260/963
[58] Field of Search ........................ 260/963; 424/224

[56] References Cited

U.S. PATENT DOCUMENTS 3,112,244  11/1963  Goyette .
3,725,546  4/1973  Tsuchiya et al. .................... 260/963

FOREIGN PATENT DOCUMENTS 1238013 of 0000 Fed. Rep. of Germany .
2232075 of 0000 Fed. Rep. of Germany .

*Primary Examiner*—Anton H. Sutto
*Attorney, Agent, or Firm*—Stevens, Davis, Miller & Mosher

[57] ABSTRACT

Nematocidal O-ethyl S-alkyl S-isopropyl phosphorodithiolates.

5 Claims, No Drawings

O-ETHYL S-ALKYL S-ISOPROPYL PHOSPHORO-DITHIOLATE, AND THEIR USE AS NEMATOCIDE

This invention relates to an O-ethyl S-alkyl S-isopropyl phosphorodithiolate represented by the general formula (I),

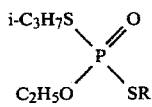
(I)

wherein R represents methyl or ethyl group. It relates also to a nematocidal composition comprising said dithiolate compound as an active ingredient.

The present compound represented by the general formula (I) is a novel nematocidal compound not described in the literature, which can control a wide variety of harmful nematoda and exhibits little phytotoxicity.

The nematocides in general use at present include D—D (a mixture of dichloropropene and dichloropropane), EDB (ethylene dibromide), DBCP (1,2-dibromo-3-chloropropane), chloropicrin and the like.

All of these chemicals diffuse as a gas through the soil and the nematoda die by contact with the gas. However, in order to ensure the nematocidal effect, covering or water sealing of the field is necessary for 7 to 14 days after application of the chemicals. Further, if a crop is transplanted or sowed while the gas is still remaining, it will suffer from chemical injury. Accordingly, the field must be left as it is for a long period after application of the chemicals or subjected to frequent degassing to remove the gas from the soil. Owing to the non-cultivation period which is required or the troublesome degassing work, an optimum sowing or planting time is often missed.

Beside the above-noted disturbance in effective utilization of the field owing to the chemical injury, a high toxicity of chloropicrin gives rise to the pollution problem and other above-noted chemicals have a disadvantage of high controlling chemical's cost per unit area.

The present inventors performed an investigation on the nematocidal effect of a series of dithiolphosphate esters and as a result found that, as will become evident from the Examples herein described, a distinguished nematocidal effect is exhibited by an ester in which the alkyl in the O-alkyl linkage is ethyl, the alkyl in one S-alkyl linkage is isopropyl, and the alkyl in the other S-alkyl linkage is methyl or ethyl, as compared with other esters having other alkyls closely related to those in the former ester. Based on this finding, the present invention has been accomplished.

The compound of this invention is a compound which is safe, free from chemical injury, applicable even during the vegetative period of the crops, is of high nematocidal activity, and of low toxicity to man and animals. As contrasted to the conventional notion about the use of commercial nematocides, the active ingredient of this invention is a distinguished nematocidal compound which is applicable to the plant at any stage of growth.

The nematocide of this invention is effective in controlling a wide variety of nematoda including not only soil nematoda such as cyst nematode, root-knot nematode and root-lesion nematode, but also other nematoda such as rice white-tip nematode.

These O-ethyl S-alkyl S-isopropyl phosphorodithiolates are synthesized as described below.

The O-ethyl S-alkyl S-isopropyl phosophorodithiolates represented by the general formula (I) can be prepared by any of the following methods A, B, C, D and E.

A. Synthesis by the reaction of a dithiophosphoric acid salt represented by the general formula (II),

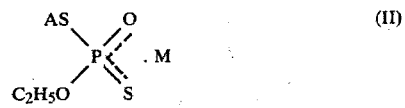
(II)

(wherein M represents an alkali metal atom such as, for example, potassium or sodium and A represents isopropyl, methyl or ethyl group) with a halide of the general formula (III),

(III)

wherein X represents a chlorine, bromine or iodine atom and B represents isopropyl, methyl or ethyl group, provided that B is methyl or ethyl group when A is isopropyl group; and B is isopropyl group when A is methyl or ethyl group.

Among the reaction conditions, the reaction temperature is from room temperature to 100° C., the reaction time is from 30 minutes to 10 hours, and the molar ratio is 1 to 2 moles of the compound represented by the formula (III) for 1 mole of the compound represented by the formula (II). The reaction solvents include alcohols such as methanol and ethanol, ketones such as acetone, nitriles such as acetonitrile, and water. When water is used as the reaction medium, the yield of the intended product can be improved by adding 0.05 mole of a phase transfer catalyst such as tetra-n-butylammonium bromide for 1 mole of the compound of the formula (II).

B. Synthesis by the reaction of a thiophosphoric acid chloride represented by the general formula (IV),

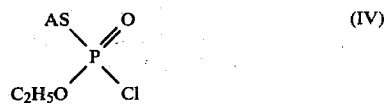
(IV)

(wherein A is as defined above) with a mercaptan of the formula (V),

(V)

(wherein B is as defined above) in the presence of an acid binding agent. As the acid binding agents, mention may be made of organic bases such as triethylamine and pyridine.

The reaction conditions are such that the reaction temperature is 0° to 100° C., the reaction time is 30 minutes to 10 hours and the molar ratio is 1 to 2 moles of the compound of formula (V) and the acid binding agent for 1 mole of the compound of formula (IV). Examples of the reaction solvents are hydrocarbons such as hexane, benzene and toluene, ethers such as ethyl ether, ketones such as acetone and methyl isobutyl ketone, esters such as ethyl acetate, nitriles such as acetonitrile, and halohydrocarbons such as methylene chloride and chloroform.

C. Synthesis by the reaction of a thiophosphoric acid chloride of the above general formula (IV) with a mercaptide of the formula (VI), $$B\text{—}SM \quad \text{(VI)}$$

wherein B and M are as defined above.

The reaction conditions are such that the reaction temperature is 0° to 100° C., the reaction time is 30 minutes to 10 hours, and the molar ratio is 1 to 1.1 moles of the compound of formula (VI) for 1 mole of the compound of formula (IV). Examples of the reaction solvents are hydrocarbons such as hexane, benzene and toluene, ethers such as ethyl ether, ketones such as acetone and methyl isobutyl ketone, esters such as ethyl acetate, nitriles such as acetonitrile and halohydrocarbons such as methylene chloride and chloroform.

D. Synthesis in two steps. In the first step, a phosphorochloridodithioite represented by the general formula (VII),

(wherein G represents methyl or ethyl group) is reacted with ethanol in the presence of an acid binding agent under a nitrogen atmosphere to synthesize a phosphorodithioite represented by the general formula (VIII),

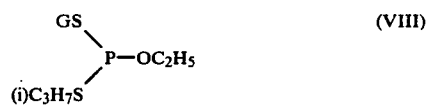

(wherein G is as defined before) and in the second step, this compound is treated with an oxidizer.

The acid binding agent used is an organic base such as triethylamine or pyridine and the oxidizer used is a peroxide such as hydrogen peroxide. The reaction conditions in the first step are such that the reaction temperature is 0° to 5° C., the reaction time is 1 to 3 hours, and the molar ratio is 1 to 1.5 moles of ethanol and the acid binding agent for 1 mole of the compound of formula (VII). The reaction solvents are hydrocarbons such as hexane and benzene, ketones such as acetone and methyl isobutyl ketone, ethers such as ethyl ether, esters such as ethyl acetate, and halohydrocarbons such as chloroform.

The reaction conditions in the second step are such that the reaction temperature is 0° to 100° C., the reaction time is 30 minutes to several hours, and the molar ratio is 1 to 1.2 moles of an oxidizer for 1 mole of the compound of formula (VII). The reaction solvents are hydrocarbons such as hexane and benzene, and halohydrocarbons such as methylene chloride.

E. Synthesis by the reaction of a phosphorochloridodithiolate represented by the formula (IX),

(wherein G is as defined above) with ethanol in the presence of an acid binding agent, or by the reaction of said compound of the formula (IX) with sodium ethylate. The acid binding agent is an organic base such as triethylamine or pyridine. The reaction conditions are such that the reaction temperature is 0° to 100° C., the reaction time is 30 minutes to 10 hours, and the molar ratio is 1 to 1.5 moles of ethanol and the acid binding agent, or 1 to 1.5 moles of sodium ethylate for 1 mole of the compound of formula (IX). The reaction solvents are hydrocarbons such as hexane, benzene, and toluene, ethers such as ethyl ether, ketones such as acetone and methyl isobutyl ketone, esters such as ethyl acetate, nitriles such as acetonitrile, and halohydrocarbons such as methylene chloride and chloroform.

| Compound No. | Structural formula | Physical constant |
|---|---|---|
| Compound (1) of this invention | i-C$_3$H$_7$S, C$_2$H$_5$O \P(=O)— S—CH$_3$ | $n_D^{26.0}$ 1.5045 |
| Compound (2) of this invention | i-C$_3$H$_7$S, C$_2$H$_5$O \P(=O)— S—C$_2$H$_5$ | $n_D^{26.0}$ 1.4948 |
| Reference compound (a) (MOCAP®) | n-C$_3$H$_7$S, C$_2$H$_5$O \P(=O)— S—C$_3$H$_{7(n)}$ | $n_D^{26.0}$ 1.5015 |
| Reference compound (b) | n-C$_3$H$_7$S, C$_2$H$_5$O \P(=O)— S—C$_3$H$_{7(i)}$ | $n_D^{26.0}$ 1.4972 |
| Reference compound (c) | n-C$_4$H$_9$S, C$_2$H$_5$O \P(=O)— S—CH$_3$ | $n_D^{26.0}$ 1.5037 |
| Reference compound (d) | n-C$_4$H$_9$S, C$_2$H$_5$O \P(=O)— S—C$_2$H$_5$ | $n_D^{26.0}$ 1.4998 |
| Reference compound (e) | i-C$_3$H$_7$S, n-C$_3$H$_7$ \P(=O)— S—CH$_3$ | $n_D^{26.0}$ 1.5015 |
| Reference compound (f) | C$_2$H$_5$—S, C$_2$H$_5$O \P(=O)— S—C$_2$H$_5$ | $n_D^{27.5}$ 1.5076 |

Typical examples of synthesis are described below.

Synthesis Example 1 [Compound (1) of this invention]

Into 100 ml of acetone, was dissolved 11.9 g of potassium O-ethyl S-isopropyl dithiophosphate. After addition of 10.6 g of methyl iodide, the solution was refluxed for one hour with stirring. The reaction mixture was stripped of the acetone under reduced pressure. The residue was dissolved in toluene, washed with a 5% aqueous sodium carbonate solution, then with water, and the toluene was removed under reduced pressure, leaving behind 8.9 g of an oily substance. This substance was subjected to silica gel column chromatography to yield 8.0 g of O-ethyl S-methyl S-isopropyl phosphorodithiolate in the form of pale yellowish green oil having a refractive index ($n_D^{26.0}$) of 1.5045.

Elementary analysis:

|  | Calculated for $C_6H_{15}O_2PS_2$ |  |
|---|---|---|
| C% | 33.63 | 33.45 |
| H% | 7.06 | 6.92 |
| P% | 14.45 | 14.28 |

Synthesis Example 2 [Compound (2) of this invention]

Into 100 ml of toluene, was dissolved 10.2 g of O-ethyl S-isopropyl thiophosphoric acid chloride followed by 4.7 g of ethyl mercaptan. To the solution was added dropwise 6.0 g of triethylamine at room temperature. After having been stirred for two hours at room temperature, the reaction mixture was washed successively with 10% hydrochloric acid, water, 5% aqueous sodium carbonate solution, and water. The toluene was removed under reduced pressure, leaving behind 8.1 g of an oily substance. This oily substance was subjected to silica gel column chromatography to obtain 6.7 g of O,S-diethyl S-isopropyl phosphorodithiolate in the form of yellowish green oil having a refractive index ($n_D^{26.0}$) of 1.4949.

Elementary analysis:

|  | Calculated for $C_7H_{17}O_2PS_2$ | Found |
|---|---|---|
| C% | 36.83 | 36.64 |
| H% | 7.51 | 7.39 |
| P% | 13.56 | 13.28 |

Synthesis Example 3 [Compound (1) of this invention]

A mixture comprising 21.0 g of a 50% aqueous solution of potassium O-ethyl S-methyl dithiophosphate, 11.1 g of isopropyl iodide and 0.8 g of tetra-n-butylammonium bromide was stirred at 50° C. for one hour. The reaction mixture was extracted with 50 ml of toluene. The extract was freed from the toluene under reduced pressure, leaving behind 9.5 g of an oily substance. This substance was subjected to silica gel column chromatography to obtain 9.0 g of O-ethyl S-isopropyl S-methyl phosphorodithiolate.

Synthesis Example 4 [Compound (2) of this invention]

To a mixture of 4.4 g of sodium ethyl mercaptide and 50 ml of methyl isobutyl ketone, was added dropwise at 0° C. 10.1 g of O-ethyl S-isopropyl thiophosphoric acid chloride. The mixture was stirred at 0° C. for one hour and treated in a manner similar to that in Synthesis Example 2 to obtain 9.1 g of O,S-diethyl S-isopropyl phosphorodithiolate.

Synthesis Example 5 [Compound (1) of this invention]

Into 20 ml of hexane, was dissolved 9.4 g of S-isopropyl S-methyl phosphorochloridodithioite. To the solution was added dropwise at 0° to 5° C. a mixture of 2.8 g of ethanol and 6.1 g of triethylamine. The resulting reactant mixture was stirred at 0° to 5° C. for 2 hours. The reaction was carried out under a nitrogen atmosphere to prevent oxidation. After removal of triethylamine hydrochloride by filtration, the filtrate was concentrated to obtain 9.4 g of O-ethyl S-isopropyl S-methyl phosphorodithioite. This product was dissolved in 20 ml of benzene and heated under reflux. To the solution, while being kept under reflux, was added dropwise 5.9 g of 30% aqueous hydrogen peroxide. The mixture was stirred at 80° C. for one hour and then left standing to cool down. The organic layer was washed twice with 20 g of a 5% aqueous sodium hydroxide solution and then twice with water. Th benzene was removed under reduced pressure, leaving behind 9.1 g of a reaction product which, on silica gel column chromatography, yielded 8.7 g of O-ethyl S-isopropyl S-methyl phosphorodithiolate.

Synthesis Example 6 [Compound (2) of this invention]

Into 30 ml of toluene, was dissolved 10.9 g of S-ethyl S-isopropyl phosphorochloridodithiolate followed by 2.5 g of ethanol. To the solution, was added dropwise at room temperature 5.6 g of triethylamine. The mixture was stirred for one hour at room temperature and then treated in a manner similar to that in Synthesis Example 2 to obtain 6.5 g of O,S-diethyl S-isopropyl phosphorodithiolate.

The compounds of this invention prepared as described above are oily substances and are formulated in a customary way by admixing with liquid, solid, or even gaseous carriers and, if necessary, various adjuvants to prepare oil sprays, emulsifiable concentrates, wettable powders, granules or ducts, which are applicable in a customary way. The compounds can, of course, be applied in admixtures with other nematocides, insecticides, herbicides, fungicides, seed disinfectants, or fertilizer, soil-improving agent.

The effectiveness of this invention is described below with reference to test examples and preparation examples. However, the active ingredients, adjuvants, preparations, etc., are, of course, not limited to those described in the examples.

The above-noted preparations in various forms generally contain 0.1 to 90% by weight of active ingredients (including active ingredients other than those of this invention) and are applied usually 25 to 500 g/10 ares. However, the application rate and concentration of the active ingredient vary with the form of preparations, stage of the plant growth, application method, locality, type of the crop, etc. Therefore, it is not necessary to stick to the above-noted range but the compound can be applied more freely without any adverse effect.

Test Example 1

Controlling effect on tomato root-knot nematode when applied at the period of growing.

A mixture of 500 g of soil infested with root-knot nematode (*Meloidgyne* sp.) and an equal amount of non-infested soil was placed in each 1/5,000-are Wagner pot and planted with each 6 tomato seedlings of 3 to 4 leaf age. Two days after the seedlings had sufficiently rooted, an emulsion of the present compound (1) or (2) prepared as described in Preparation Example 1 was drenched over the soil at a rate of 80 ml/pot (4 liters/m²). For comparison, other pots were similarly treated using DSCP and the compounds (a) to (f).

After 21 days from the soil treatment, growth of the tomato plant and the formation of root knot were observed and recorded according to the following criteria. Each test was repeated three times.

| Formation of root knot | |
|---|---|
| Rating | Degree of formation of root knot |
| 0 | The same as in untreated, non-infested soil (i.e. no formation of root knot). |

-continued

Formation of root knot

| Rating | Degree of formation of root knot |
| --- | --- |
| 1 | Slight knot formation, as compared with untreated, non-infested soil. |
| 2 | Distinctive knot formation as compared with untreated, non-infested soil. |
| 3 | Formation of a large number of root knots approximating to that in untreated, infested soil. |
| 4 | Formation of root knots, in number comparable to or more than that in untreated, infested soil. |

Growth of plant

| Rating | Degree of growth of tomato seedling |
| --- | --- |
| A | The same as or better than the seedling in non-infested soil. |
| B | Slightly inferior to the seedling in non-infested soil. |
| C | Distinctively inferior to the seedling in non-infested soil. |
| D | Majority of seedlings withered or markedly undergrown. |

The test results were as shown in Table 1.

TABLE 1

| Test compound | Concentration of compound (ppm) | Root knot formation | Growth of tomato seedling |
| --- | --- | --- | --- |
| Compound (1) of this invention | 250 | 0 | A |
|  | 125 | 0 | A |
| Compound (2) of this invention | 250 | 0 | B |
|  | 125 | 0 | A |
| Reference compound (a) | 250 | 2 | B |
|  | 125 | 3 | B |
| Reference compound (b) | 250 | 4 | B |
| Reference compound (c) | 250 | 4 | B-C |
| Reference compound (d) | 250 | 3 | C |
|  | 125 | 3 | B |
| Reference (f) | 250 | 4 | B-C |
| compound DBCP | 500 | 2 | C |

Test Example 2

Controlling effect on tomato root-knot nematode when applied at the time of transplanting.

A mixture of 500 g of soil infested with root-knot nematode (*Meloidgyne* sp.) and an equal amount of non-infested soil was placed in each 1/5,000-are Wagner pot. A granule preparation containing the compound (1) or (2) of this invention, prepared as described in Preparation Example 3, was added to the pot at a rate of 0.2 g/pot (1 kg/are) and uniformly mixed with the soil in the upper depth of 15 cm. Six tomato seedlings of 3 to 4 leaf age were then transplanted to each pot. For comparison, other pots were similarly treated using as reference a diluted DBCP emulsion and granules containing the compounds (a), (c) and (e).

After 21 days from the soil treatment, growth of the tomato plant and the formation of root knots were observed and recorded in the same manner as in Test Example 1. Each test was repeated three times. The test results were as shown in Table 2.

TABLE 2

| Test compound | Amount of preparation (kg/are) | Root knot formation | Growth of tomato seedling |
| --- | --- | --- | --- |
| Compound (1) of this invention | 1 (0.05) | 0 | A |
| Compound (2) of this invention | 1 (0.05) | 1 | A |
| Reference compound (a) | 1 (0.05) | 3 | B |
| Reference compound (c) | 1 (0.05) | 4 | B |
| Reference compound (e) | 1 (0.05) | 4 | C |
| Reference compound DBCP | 500 ppm | 1 | C |

Note:
Figures in parentheses are the amounts applied of active compounds.

In all of the test plots treated with the compound (1) or (2) of this invention, substantially no root knot was found and the growth of tomato seedling was also good, the test results having been distinctively superior to those in the reference plots.

Test Example 3

Controlling effect on soybean cyst nematode when applied at the time of seeding.

A mixture of 500 g of soil infested with soybean cyst nematode (*Heterodera glycines*) and an equal amount of non-infested soil was placed in each 1/5,000-are Wagner pot. After the emulsion containing the compound (1) or (2) of this invention, prepared as described in Preparation Example 1, had been sprayed over the soil at a rate of 80 ml/pot and uniformly mixed with the soil in the upper depth of 15 cm, 10 soybeans were seeded in each pot. For comparison, the same soil mixture as used above was treated with a DBCP emulsion or the reference compound (a).

After 30 days from the chemical treatment, the growth of each soybean plant and the cyst adhesion were inspected. The results of inspection were recorded in the same manner as in Test Example 1. Each test was repeated three times. The test results were as shown in Table 3.

TABLE 3

| Test compound | Concentration of preparation (ppm) | Adhesion of cyst | Growth of soybean plant |
| --- | --- | --- | --- |
| Compound (1) of this invention | 100 | 0 | A |
| Compound (2) of this invention | 100 | 0 | B |
| Reference compound (a) | 100 | 3 | B-C |
| Reference compound DBCP | 500 | 2 | B |

Test Example 4

Controlling effect on root-lesion nematode by application at the time of seeding.

A mixture of 500 g of soil infested with root-rod nematode (*Pratylenchus* sp.) and an equal amount of uninfested soil was placed in each 1/5,000-are Wagner pot. The pot was applied with 0.2 g/pot (1 kg/are) of a dust preparation of the compound (1) or (2) of this invention. After the dust had been uniformly mixed with the soil in the upper depth of 15 cm, 15 carrot seeds were sowed in each pot. For comparison, the same soil mixture as used above was treated with a DBCP emulsion or the reference compound (d).

After 60 days from the chemical treatment, the growth of each carrot and the development of root-lesion disease spots were inspected. The inspection results were recorded in the same manner as in Test Example 1. Each test was repeated four times. The test results were as shown in Table 4.

TABLE 4

| Test compound | Concentration of preparation (ppm) | Development of lesion spot | Growth of carrot |
| --- | --- | --- | --- |
| Compound (1) of this invention | 100 | 0 | A |
| Compound (2) of this invention | 100 | 0 | A |
| Reference compound (d) | 100 | 4 | B |
| Reference compound DBCP | 500 | 1 | B |

Test Example 5

A field with the soil infested with root-knot nematode (*Meloidgyne* sp.) was divided by plastic plates into test plots, each 2 m × 1 m in area. An oil spray preparation containing the compound (1) or (2) of this invention, prepared as described in Preparation Example 5, was injected into the test plot soil at the points 20 cm apart from each other and at a depth of 15 cm. The injected amount of the preparation was 2 ml for each point (about 5 liters/are). The injected spots were covered with soil and left as such for 5 days. Thereafter, 20/m² of tomato seedlings of 3 to 4 leaf age were transplanted at uniform intervals. After 28 days from the tranplanting, tomato plants were collected and inspected for the growth. It was found that the growth in each test plot was comparable to that in the control plot where the soild had been uninfested. The number of root knots in the test plots was zero or several at most. On the contrary, in the plot where the soil was infested and not subjected to the chemical treatment, the growth of tomato plant in both plant height and root length was much retarded and the formation of a large number of root knot was observed.

Preparation Example 1

Into 50 parts of xylene, was dissolved 40 parts of the compound (1) or (2) of this invention. The resulting solution was admixed with 10 parts of an emulsifier, Sorpol SM-200 (trademark for Toho Chemical Co.; a mixture of anionic and nonionic surface active agents) and stirred thoroughly to obtain a 40% emulsifiable concentrate.

Preparation Example 2

To 40 parts of the compound (1) or (2) of this invention, was added with stirring 75 parts of Sorpol SM-200 (the same as described above). To the resulting uniform mixture, were added successively 20 parts of carplex #80 (trademark for Shionogi and Co., a fine powder of synthetic hydrated silicon oxide) and 35 parts of 300-mesh diatomaceous earth. The mixture was passed through a commercial liquidizer to obtain a 40% wettable powder.

Preparation Example 3

To 5 parts of the compound (1) or (2) of this invention, were added 5 parts of Toyolignin CT (trademark for Toyobo Co.; a lignin sulfonate) and 90 parts of GSM Clay (trademark for Zieklite Kogyo Co.). The mixture was thoroughly blended by means of an attrition mill. After addition of 10% of water, the mixture was further stirred, then granulated by means of a granulator, and dried under the air current to obtain a 5% granule preparation.

Preparation Example 4

Into 20 parts of acetone, was dissolved 5 parts of the compound (1) or (2) of this invention. To the mixture, were added successively 3 parts of carplex #80 (the same as mentioned before), 0.3 part of PAP (isopropyl hydrogenphosphate) and 91.7 parts of 300-mesh talc. The mixture was thoroughly blended by means of a liquidizer and stripped of the acetone by evaporation to obtain a 5% dust preparation.

Preparation Example 5

A 20% oil spray preparation was obtained by dissolving 20 parts of the compound (1) or (2) of this invention in kerosene to make up a total of 100 parts.

What is claimed is:

1. An O-ethyl S-alkyl S-isopropyl phosphorodithiolate of the formula (I),

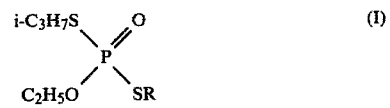

wherein R is methyl or ethyl group.

2. A compound according to claim 1 wherein R is methyl.

3. A method for controlling a nematode with a nematocidally effective amount of a compound according to claim 1.

4. A nematocidal composition comprising an inert carrier and as the active ingredient a nematocidally effective amount of a compound according to claim 1.

5. A nematocidal composition comprising an inert carrier and as the active ingredient a nematocidally effective amount of a compound according to claim 2.

* * * * *